US00PP31387P3

(12) United States Plant Patent
Suphachadiwong

(10) Patent No.: US PP31,387 P3
(45) Date of Patent: Jan. 21, 2020

(54) ***VANDA* PLANT NAMED 'SPCDW1711'**

(50) Latin Name: ***Vanda* spp. Jones ex R. Br.**
Varietal Denomination: SPCDW1711

(71) Applicant: Suphatchatwong Innovation Co., Ltd., Chonburi (TH)

(72) Inventor: Thumrong Suphachadiwong, Bangphra (TH)

(73) Assignee: Suphatchatwong Innovation Co., Ltd., Chonburi (TH)

( * ) Notice: Subject to any disclaimer, the term of this patent is extended or adjusted under 35 U.S.C. 154(b) by 0 days.

(21) Appl. No.: 16/350,784

(22) Filed: Jan. 14, 2019

(65) Prior Publication Data

US 2019/0223356 P1 Jul. 18, 2019

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
See application file for complete search history.

(56) References Cited

PUBLICATIONS

PLUTO Plant Variety Database Jul. 31, 2019.*

* cited by examiner

*Primary Examiner* — Annette H Para
(74) *Attorney, Agent, or Firm* — Samuel R. McCoy, Jr.

(57) ABSTRACT

A new and distinct *Vanda* plant named 'SPCDW1711' which is characterized by large flowers with a distinct color contrast between the upper and lower half of the flower, with a purple dorsal sepal and purple lateral petals which is contrasted by dark greyed-purple lateral sepals, lateral sepals which fade lighter towards the margins to reveal dark greyed-purple reticulate veining, a labellum with a very dark greyed-purple central lobe and yellow-green lateral lobes which are radially striped with red-purple, and the stability of these characteristics from generation to generation.

4 Drawing Sheets

Latin name of the genus and species: The Latin name of the genus and species of the novel variety disclosed herein is *Vanda* spp. Jones ex R. Br.

Variety denomination: The inventive variety of *Vanda* disclosed herein has been given the variety denomination 'SPCDW1711'.

CROSS REFERENCE TO RELATED APPLICATIONS

This application claims priority to the Community Plant Variety Rights application number 2018/0176, filed Jan. 16, 2018, which is herein incorporated by reference.

BACKGROUND OF THE INVENTION

Parentage: The new *Vanda* plant, 'SPCDW1711', is the result of a planned breeding program. 'SPCDW1711' originated as a seedling from the controlled pollination of *Vanda* 'QT' (not patented), the seed parent, with *Vanda* 'S60' (not patented), the pollen parent. Both parents were developed by, and are owned by, the inventor and were never commercially released. The crossing was made by the inventor in his research greenhouse in Bangphra, Thailand in August of 1994.

The new variety was first selected in January of 1999, in a research greenhouse in Bangphra, Thailand belonging to the inventor. After identifying the new variety as a potentially interesting selection, the inventor continued confidential testing and propagation of 'SPCDW1711', assessing stability of the unique characteristics of this variety.

Asexual Reproduction: Asexual January of 2011 at a commercial laboratory belonging to the inventor in Bangphra, Thailand. Access to all plants was restricted, as plants were kept in a greenhouse not open to the public, and tissue culture plantlets were in a laboratory belonging to the inventor, and not accessible to the public. Through six subsequent generations, the unique features of this cultivar have proven to be stable and true to type.

SUMMARY OF THE INVENTION

The cultivar 'SPCDW1711' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SPCDW1711'. These characteristics in combination distinguish 'SPCDW1711' as a new and distinct *Vanda* cultivar:

1. *Vanda* 'SPCDW1711' exhibits relatively large flowers borne on an inflorescence which is carried slightly above the foliage; and
2. *Vanda* 'SPCDW1711' exhibits a distinct color contrast between the upper half of the flower, comprised of the dorsal sepal and lateral petals, and the lateral sepals; and 3. *Vanda* 'SPCDW1711' exhibits a purple dorsal sepal and purple lateral petals which are blotched and finely dotted with dark greyed-purple at the base; and
4. *Vanda* 'SPCDW1711' exhibits dark greyed-purple lateral sepals which fade lighter towards the margins to reveal the dense, dark greyed-purple reticulate veining; and
5. *Vanda* 'SPCDW1711' exhibits a labellum with a very dark greyed-purple central lobe, and yellow-green lateral lobes which are radially striped with red-purple.

BOTANICAL DESCRIPTION OF THE PLANT

Figure 1:
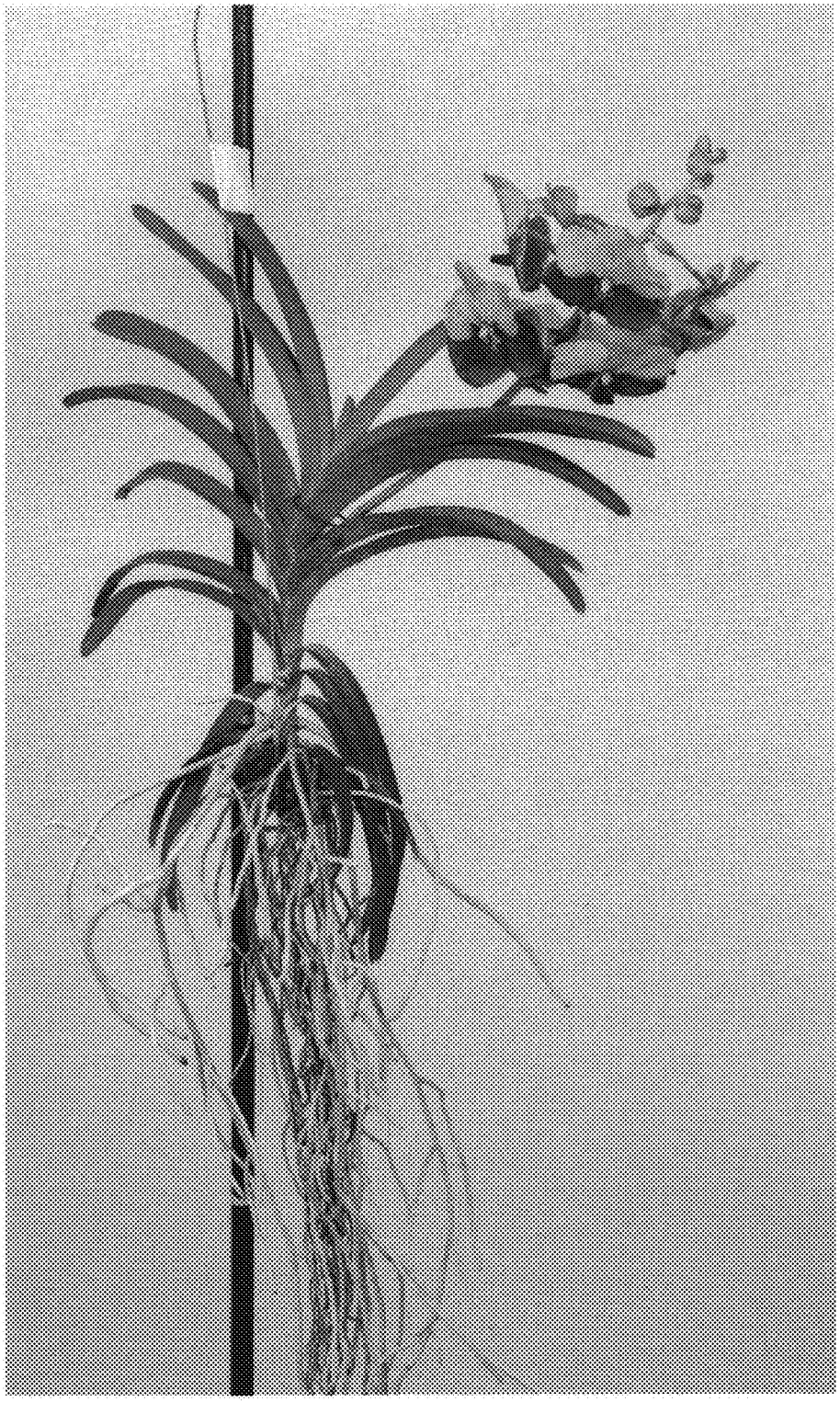
FIG. 1 illustrates, as nearly true as it is reasonably possible to make the same in color photographs of this type, an exemplary plant of 'SPCDW1711' grown in a commercial greenhouse in Honselersdijk, the Netherlands. This plant is approximately 6 years old from the time of meri-cloning, shown planted in an 8 by 2 cm container.
Figure 2:
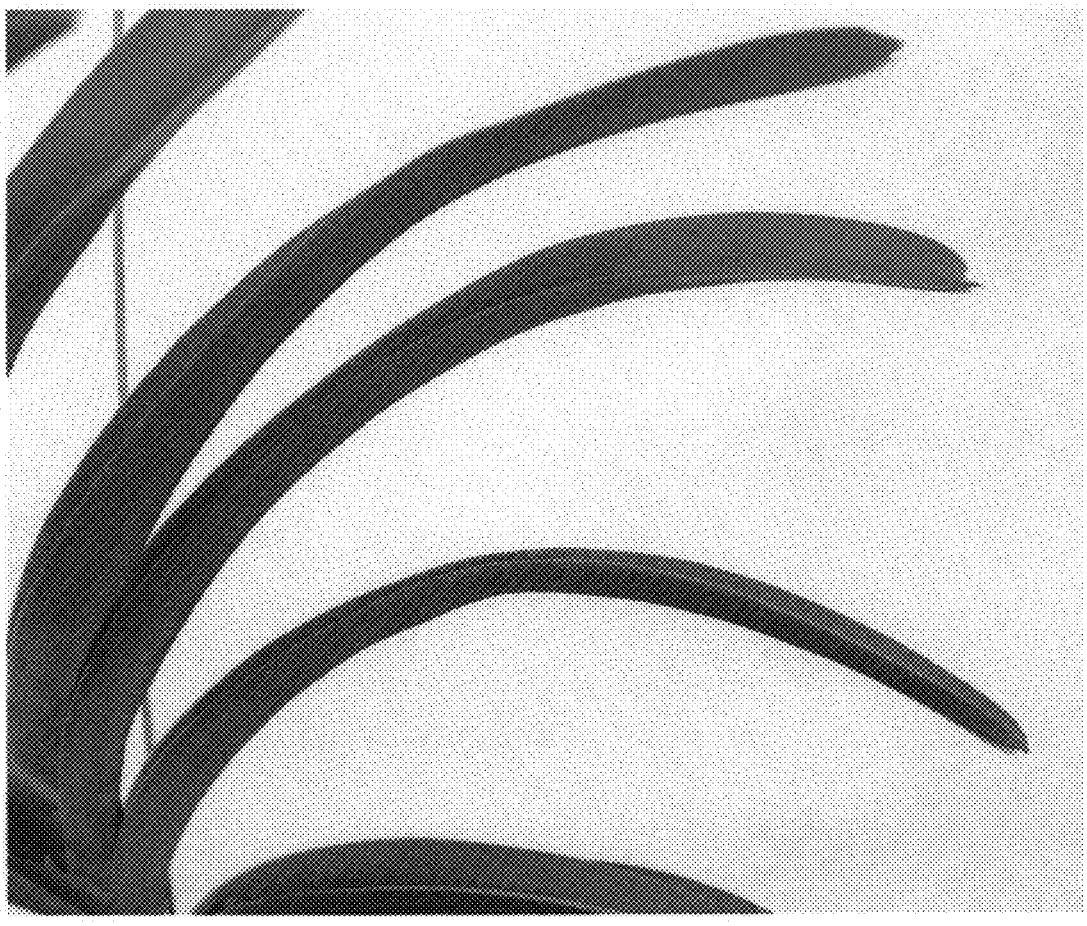
FIG. 2 illustrates, as nearly true as it is reasonably possible to make the same in color photographs of this type, the typical foliage of 'SPCDW1711'.
Figure 3:
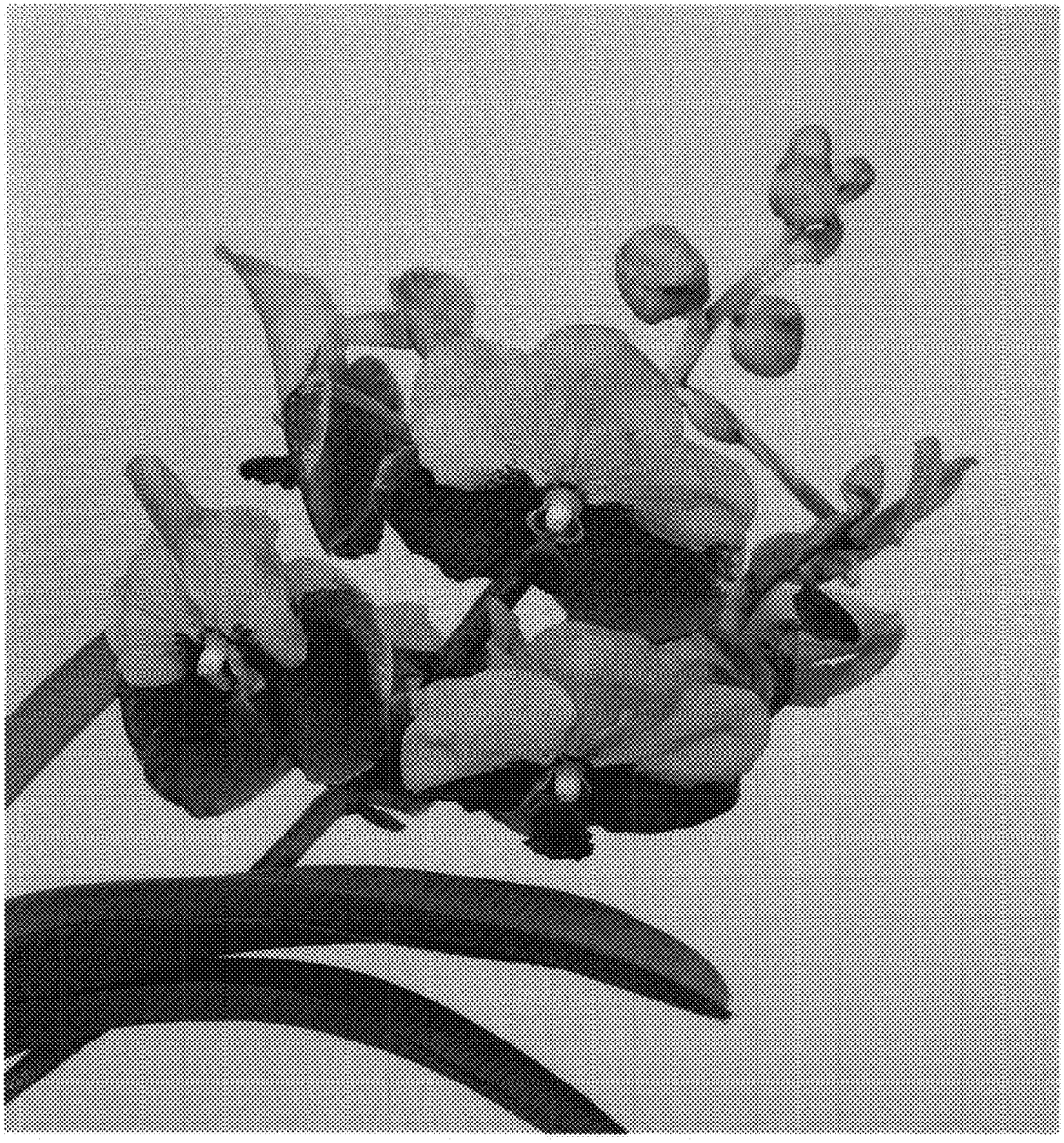
FIG. 3 illustrates, as nearly true as it is reasonably possible to make the same in color photographs of this type, the typical inflorescence of 'SPCDW1711'.
Figure 4:
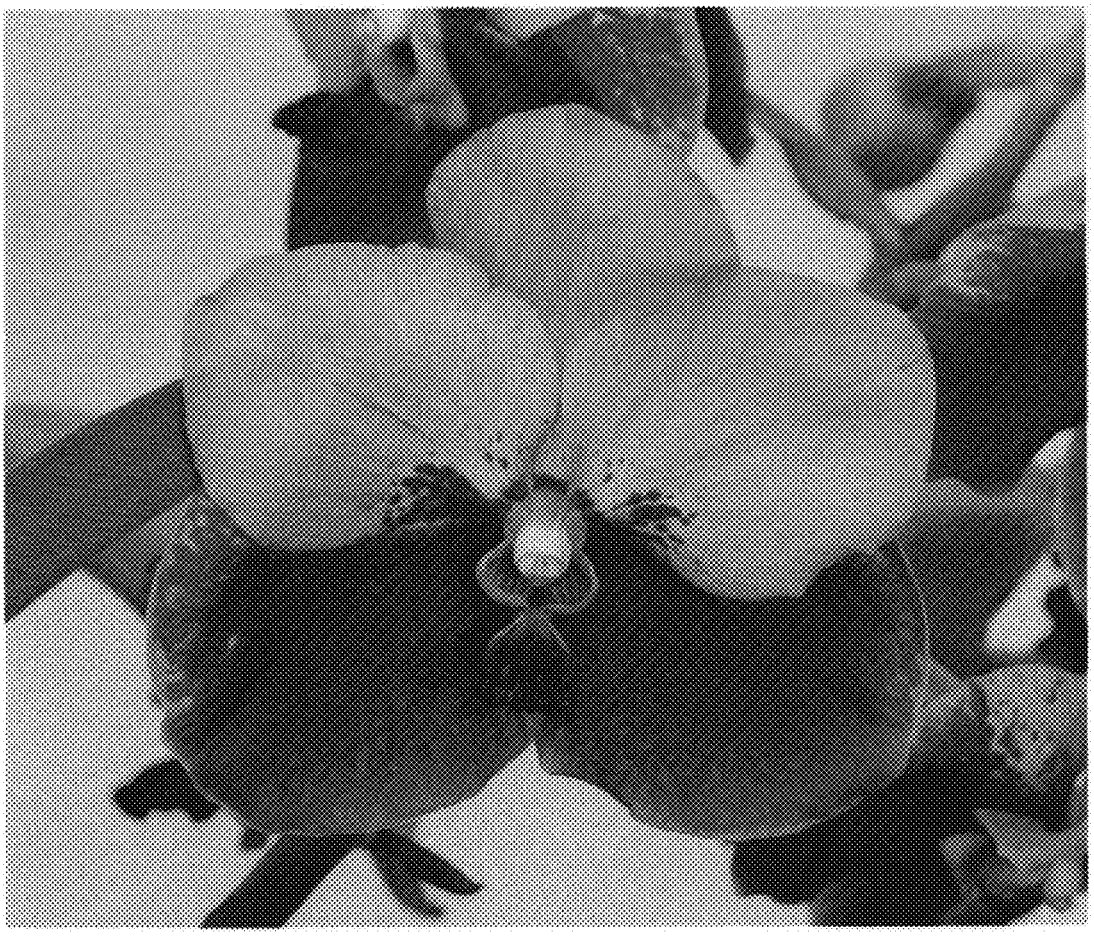
FIG. 4 illustrates, as nearly true as it is reasonably possible to make the same in color photographs of this type, the typical flower of 'SPCDW1711'.

The following observations and measurements made in August of 2018 describe averages from a sample set of six specimens of six year-old 'SPCDW1711' plants grown in a greenhouse in Honselersdijk, the Netherlands. Temperatures were approximately 23 degrees Celsius during the day and 19 degrees Celsius at night. No photoperiodic or chemical treatments were given to the plants. No artificial light was given to the plants.

Those skilled in the art will appreciate that certain characteristics will vary with older or, conversely, with younger plants. 'SPCDW1711' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'SPCDW1711' and comparisons with the parents and most similar commercial variety of *Vanda* are provided below.

Plant description:

*Growth habit.*—Perennial; monopodial, upright. Single monopodial leafy stem, with flowers carried above the leaf plane; inflorescences growing from the leaf axils.

*Average height from base (plant grown in hanging basket, so no soil line present) to foliar plane.*—42.0 cm.

*Average height from base (plant grown in hanging basket, so no soil line present) to top of floral plane.*—48.8 cm.

*Plant spread.*—Average of 45.5 cm.

*Appropriate container size.*—8 cm by 2 cm rectangular hanging basket.

*Growth rate.*—Moderate.

*Plant vigor.*—Moderate.

*Propagation type.*—Meristematic tissue culture propagation using the base of the leaves.

*Propagation details.*—The time needed from for the start of a mericlone to get the small plants ready for deflasking is approximately 24 months under a controlled temperature of about 26 degrees Celsius. After that period, plants have matured roots. Plants start to make roots in the last 6 months in flasks. After deflasking they remain in a shaded and controlled environment.

*Disease and pest resistance or susceptibility.*—Plants have not been observed to be susceptible or resistant to pathogens and pests common to *Vanda*.

*Environmental tolerances.*—Adapt to, at least, USDA Zones 11 and 12 and temperatures as high as 40 degrees Celsius; high tolerance to rain; moderate to high tolerance to wind.

Root system:

*General.*—Moderately to densely rooting; with aerial roots only.

*Dimensions, mature roots.*—66.4 cm long with a diameter of 0.5 cm, on average.

*Texture.*—Very fleshy; non-fibrous.

*Color.*—Greyed-green, nearest to RHS 192C; root apex is yellow-green, RHS 148A.

Stem:

*Branching habit.*—Monopodial; no lateral branches present.

*Number of primary (main) stems per plant.*—One.

*Number of secondary (lateral) branches per plant.*—None.

*Aspect.*—Circular, formed by the leaf sheaths.

*Length.*—20.0 cm.

*Diameter.*—1.2 cm.

*Internode length.*—1.1 cm.

*Luster.*—Matte.

*Attitude, main stem.*—Near vertical.

*Strength.*—Very strong.

*Color, juvenile.*—Nearest to in between yellow-green and green-white, RHS 145D and 157A.

*Color, mature.*—Nearest to in between yellow-green and green-white, RHS 150D and 157A.

*Color at internodes.*—Greyed-orange, nearest to a mixture of RHS 164B and 164C.

*Pubescence.*—Glabrous.

Foliage:

*Arrangement.*—Distichous.

*Dimensions.*—26.5 cm long, excluding the sheath, and 2.6 cm wide.

*Shape of blade.*—Ligulate.

*Aspect.*—Moderately to strongly carinate and lightly curled downward.

*Apex.*—Unequal praemorse.

*Base.*—Sheathing.

*Sheath dimensions.*—3.3 cm long and 1.6 cm wide, on average.

*Sheath color.*—Yellow-green, nearest to RHS 146C.

*Margin.*—Entire.

*Pubescence, texture and luster of adaxial surface.*—Glabrous, smooth, and matte.

*Pubescence, texture and luster of abaxial surface.*—Glabrous, smooth, and matte.

*Color.*—Juvenile foliage, adaxial surface — Yellow-green, nearest to RHS 144B; darker towards the apex, nearest to in between RHS 144A and 146C. Juvenile foliage, abaxial surface — Yellow-green, nearest to RHS 144B; darker towards the apex, nearest to in between RHS 144A and 146B. Mature foliage, adaxial surface — Green, nearest to RHS 137B; margined a darker shade of green, nearest to RHS NN137B. Mature foliage, abaxial surface — Yellow-green, nearest to in between RHS 144A and 146B; margined a darker shade of green, nearest to RHS NN137B.

*Venation.*—Pattern — Parallel. Color, adaxial surface — Yellow-green, nearest to RHS 146B. Color, abaxial surface — Yellow-green, nearest to in between RHS 144A and 144B.

*Petiole.*—No petioles present; leaves sessile.

Inflorescence:

*Inflorescence arrangement.*—Axially placed raceme.

*Natural flowering season.*—Autumn into winter.

*Time to flower.*—Approximately 10 months.

*Flowers per inflorescence.*—Average of 13.

*Flowers per plant.*—8 open flowers and 5 flower buds.

*Inflorescence height.*—Approximately 25.0 cm (measured from base of lowest flower to top of upper flower).

*Inflorescence diameter.*—Approximately 20.8 cm.

*Peduncle.*—Dimensions — Approximately 43.5 cm long and 0.7 cm wide. Attitude — Generally at a 25 degree angle to lateral branch axis. Strength — Moderately strong. Texture and luster — Glabrous and malle. Color — Yellow-green, nearest to in between RHS 144A and 144B.

Bud:

*Length.*—Average of 1.8 cm.

*Diameter.*—Average horizontal diameter is 1.7 cm; the vertical diameter is 1.8 cm.

*Shape.*—Cubic, with a deltoid apex which is pointed downward.

*Pubescence, texture and luster.*—Glabrous, smooth and matte.

*Color, upper surface.*—Yellow-green, nearest to in between RHS 145B and 145C, and suffused with purple, nearest to RHS N77D.

*Color, lower surface.*—Yellow-green, nearest to RHS 146D.

Flower:

*Flower type.*—Zygomorphic (orchidaceous), typical shape for the genus *Vanda*.

*Flowering habit.*—Moderately free flowering.

*Shape.*—Zygomorphic, single; consisting of three sepals and three petals, one of which is transformed into a labellum; the two lateral petals strongly overlap the dorsal and lateral sepals; lateral sepals slightly overlap one another.

*Attitude.*—Flowers are outward-facing to slightly nodding.

*Vertical height.*—Approximately 9.9 cm.

*Diameter.*—Approximately 9.8 cm.

*Depth.*—Approximately 3.8 cm.

*Fragrance.*—No fragrance.

*Lastingness.*—3 weeks, on average.

*Persistent.*—Self-cleaning.

*Petals.*—Quantity of Petals — Three unfused petals; two conventional petals and one labellum. Arrangement — One lateral petal on each side. Length — Approximately 4.9 cm. Width — Approximately 4.4 cm. Shape — Broad ovate. Apex — Obtuse. Base — Cuneate. Margin — Entire; moderately undulated. Pubescence, texture and luster of upper surface — Glabrous, velvety and matte. Pubescence, texture and luster of lower surface — Glabrous, velvety and matte. Color when opening, upper surface — Purple, nearest to a mixture of RHS N75A, N78C and N78D, and proximally suffused with greyed-yellow, nearest to in between RHS 161B and 161C; the base of the petals are irregularly blotched and finely dotted with a mixture of red-purple to greyed-purple, RHS 59A and 187A. Color when opening, lower surface — Purple, nearest to a mixture of RHS N75A and N78D, and becoming yellow-green at the base, nearest to RHS 145D. Color when fully opened, upper surface — Purple, nearest to a mixture of RHS N75A, N78C and N78D, and proximally suffused with greyed-yellow, nearest to RHS 161B; the base of the petals are irregularly blotched and finely dotted greyed-purple, RHS 187A. Color when fully opened, lower surface — Purple, nearest to a mixture of RHS N75A and N78D, and becoming yellow-green at the base, nearest to RHS 145D. Fading, upper surface — Not fading. Fading, lower surface — Not fading. Venation — Densely reticulate on the upper surface; only the main vein is visible on the lower surface. Venation color, fully opened, upper surface — Purple, nearest to a mixture of RHS N75A, N78C and N78D, and proximally suffused with greyed-yellow, nearest to RHS 161B; the base of the petals are irregularly blotched and finely dotted greyed-purple, RHS 187A; main vein is purple, nearest to RHS NN78D. Venation color, fully opened, lower surface — Purple, nearest to a mixture of RHS N75A and N78D, and becoming yellow-green at the base, nearest to RHS 145D; main vein is purple, nearest to RHS NN78D.

*Labellum.*—Shape — Three-lobed; the shape of the lateral lobes is obovate, and the aspect is involute; the shape of the central lobe Is broad ovate, and the aspect is moderately convex. Length — Central lobe — Approximately 2.0 cm. Lateral lobes — Approximately 0.8 cm. Width — Central lobe — Approximately 1.5 cm at the base; 1.3 at the apex. Lateral lobes — Approximately 0.7 cm. Apex — Central lobe — Obtuse. Lateral lobes — Obtuse. Base — Central lobe — Cuneate. Lateral lobes — Cuneate. Margin — Central lobe — Entire; strongly undulated. Lateral lobes — Entire; not undulated. Texture and luster of upper surface — Central lobe — Glabrous, velvety, and matte with a glossy apex. Lateral lobes — Glabrous, velvety, and matte. Texture and luster of lower surface — Central lobe — Glabrous, velvety, and matte with a moderately glossy apex. Lateral lobes — Glabrous, velvety, and matte. Color when opening, upper surface — Central lobe — Nearest to a mixture of red-purple and greyed-purple, RHS 59A and N186D, and becoming greyed-purple distally, nearest to RHS N186C. Lateral lobes — Yellow-green, nearest to RHS 151D, and radially striped red-purple, nearest to a mixture of RHS 59A and 59B. Color when opening, lower surface — Central lobe — Nearest to greyed-purple, N186D, and becoming darker, distally, nearest to RHS 187A. Lateral lobes — Yellow-green, nearest to RHS 151D, and radially striped greyed-red, nearest to a mixture of RHS 178A and 178B. Color when fully opened, upper surface — Central lobe — Greyed-purple, nearest to in between RHS N186D and 187B, and becoming darker, distally, nearest to RHS N186C. Lateral lobes — Yellow-green, nearest to RHS 151D, and radially striped red-purple, nearest to a mixture of RHS 59A and 59B. Color when fully opened, lower surface — Central lobe — Purple, nearest to RHS N79B, and becoming greyed-purple, distally, nearest to RHS 187A. Lateral lobes — Yellow-green, nearest to RHS 151D, and radially striped greyed-red, nearest to a mixture of RHS 178A and 178B. Fading, upper surface — Not fading. Fading, lower surface — Not fading. Venation — No visible venation. Venation color, fully opened, upper surface — Central lobe — No visible venation. Lateral lobes — No visible venation. Venation color, fully opened, lower surface — Central lobe — No visible venation. Lateral lobes — No visible venation.

*Callosities.*—Dimensions — 1.6 cm long and 0.6 cm wide, on average. Color — Nearest to in between purple and greyed-purple, RHS N79A and 187A, and fading to greyed-purple towards the apex, nearest to RHS N186B.

*Spurs.*—Quantity — Average of 1. Length — Approximately 0.5 cm. Diameter — Approximately 0.4 cm. Vertical height — Approximately 0.7 cm, at the base. Shape — Short triangular; flattened. Apex — Bluntly acute. Base — Broad cuneate. Pubescence, texture and luster — Glabrous, smooth, and matte. Color — Greyed-green, nearest to RHS 196B, and radially striped with a darker shade of greyed-green, nearest to RHS 195B.

*Sepals.*—Quantity — Average of 3 unfused sepals. Arrangement — One dorsal sepal and two lateral sepals. Length — Dorsal sepal — Approximately 5.0 cm. Lateral sepals — Approximately 5.8 cm. Width — Dorsal sepal — Approximately 4.5 cm. Lateral sepals — Approximately 6.3 cm. Shape — Dorsal sepal — Broad ovate to broad oblong. Lateral sepals — Reniform. Apex — Dorsal sepal — Obtuse. Lateral sepals — Obtuse. Base — Dorsal sepal — Cuneate. Lateral sepals — Cuneate. Margin — Dorsal sepal — Entire; moderately finely undulated. Lateral sepals — Entire; not undulated. Pubescence, texture and luster, upper surface — Dorsal sepal — Glabrous, velvety, and matte. Lateral sepals — Glabrous, velvety, and matte. Pubescence, texture and luster, lower surface — Dorsal sepal — Glabrous, velvety, and matte. Lateral sepals — Glabrous, velvety, and matte. Color when opening, upper surface — Dorsal sepal — Purple, nearest to a mixture of RHS 77B, N78C and N78D; base is greyed-purple, nearest to RHS186. Lateral sepals — Greyed-purple, nearest to in between RHS 183A and N186C; fading to a lighter shade of greyed-purple towards the lower margins, nearest to RHS 183C, and becoming purple towards the upper margins, nearest to a mixture of RHS N75A and N78D. Color when opening, lower surface — Dorsal sepal — Nearest to a mixture of purple and purple-violet, RHS N78D, N80B and N80C. Lateral sepals — Lower half of sepals are colored greyed-yellow, nearest to RHS 161A, with greyed-orange reticulate veining, nearest to in between RHS 177B and 177C; upper half of the lateral sepals is colored purple, nearest to RHS N75A. Color when fully opened, upper surface — Dorsal sepal — Purple, nearest to a mixture of RHS 77B, N78C and N78D; base is greyed-purple, nearest to RHS186C; finely dotted red-purple towards the base, RHS 71B. Lateral sepals — Nearest to in between greyed-purple and brown, RHS N186C and 200B but closest to N186C; becoming greyed-red towards the lower margins, nearest to RHS 182B, with greyed-purple reticulate veining, nearest to RHS 183A; becoming a lighter shade of greyed-purple towards the upper margins, nearest to RHS 181D, and dotted greyed-purple, nearest to RHS 183A. Color when fully opened, lower surface — Dorsal sepal — Nearest to a mixture of purple and purple-violet, RHS N78D and N80B. Lateral sepals — Greyed-orange, nearest to RHS 176B, and suffused with greyed-purple towards the upper margin, nearest to RHS 186C. Fading, upper surface — Not fading. Fading, lower surface — Not fading. Venation — Densely reticulate. Venation color, fully opened, upper surface — Dorsal sepal — Purple, nearest to a mixture of RHS 77B and N78C; base is greyed-purple, nearest to RHS N186C; finely dotted red-purple towards the base, RHS 71B. Lateral sepals — Nearest to in between greyed-purple and brown, RHS N186C and 200B but closest to N186C; becoming greyed-red towards the lower margins, nearest to RHS 182B, with greyed-purple reticulate veining, nearest to RHS 183A; becoming a lighter shade of greyed-purple towards the upper margins, nearest to RHS 181D, and dotted greyed-purple, nearest to RHS 183A. Venation color, fully opened, lower surface — Dorsal sepal — Purple-violet, nearest to RHS N80B. Lateral sepals — Greyed-orange, nearest to RHS 176B, and suffused with greyed-purple towards the upper margin, nearest to RHS 186C.

*Pedicels.*—Length — Approximately 6.8 cm. Diameter — Approximately 0.5 cm. Attitude — Approximately 85 degree angle to peduncle axis. Strength — Moderate. Texture — Glabrous, axially angled with 5 "ribs", axially twisted (due to resupination). Luster — Glossy. Color — Purple, nearest to RHS N78B, and fading to a lighter shade of purple towards the proximal end, nearest to RHS N75A.

*Bract.*—Quantity — One bract present at the base of each pedicel. Shape — Broad ovate; folded around the base of each pedicel. Dimensions — Average of 2.0 cm long and 1.8 cm wide. Apex — Broad, bluntly acute. Base — Broad cuneate. Margins — Entire. Color, inner surface — Yellow-green, nearest to RHS 145A, and suffused and veined purple at the base, nearest to RHS 178B. Color, outer surface — Yellow-green, nearest to RHS 145A, and suffused and veined purple at the base, nearest to RHS 178B.

Reproductive organs:

*Column.*—Length — Approximately 0.8 cm. Diameter — Approximately 0.7 cm. Color — Greyed-yellow, nearest to RHS 160B; base is purple, nearest to RHS N77B.

*Ovary.*—Position — Inferior. Diameter — Approximately 0.2 cm. Color — Yellow-green, nearest to RHS 150D.

*Pollinia color.*—Yellow-orange, nearest to RHS 14A.

Seed and fruit: No fruit and seed production has been detected to date.

COMPARISON WITH THE PARENT PLANTS

Plants of the new cultivar 'SPCDW1711' differ from the *Vanda* seed parent, 'QT' (not patented), by the characteristics described in Table 1.

TABLE 1

| Characteristic | 'SPCDW1711' | 'QT' |
|---|---|---|
| Rate of growth. | Slower than 'QT'. | Faster than 'SPCDW1711'. |
| Plant size. | Larger than 'QT'. | Smaller than 'SPCDW1711'. |
| Quantity of flowers per inflorescence. | Fewer flowers than 'QT'. | More flowers than 'SPCDW1711'. |
| Flower size. | Larger than 'QT'. | Smaller than 'SPCDW1711'. |
| General coloration of the petals and sepals when fully opened. | Distinct color contrast between the upper half of the flower, comprised of the dorsal sepal and lateral petals, and the lateral sepals. | No such distinct color contrast between the upper and lower half of the flower. |

Plants of the new cultivar 'SPCDW1711' differ from the *Vanda* pollen parent, *Vanda* 'S60' (not patented), by the characteristics described in Table 2.

TABLE 2

| Characteristic | 'SPCDW1711' | 'S60' |
|---|---|---|
| Vigor; rate of growth. | Easier to propagate and faster growing than 'S60'. | More difficult to propagate and slower growing than 'SPCDW1711'. |
| Growth habit. | More compact than 'S60'. | Less compact than 'SPCDW1711'. |

TABLE 2-continued

| | | |
|---|---|---|
| Flower size. | Smaller than 'S60'. | Larger than 'SPCDW1711'. |
| Inflorescence height. | Shorter than 'S60'. | Taller than 'SPCDW1711'. |
| General coloration of the petals and sepals when fully opened. | Colored darker. | Colored lighter. |

COMPARISON WITH THE MOST SIMILAR *VANDA* CULTIVAR KNOWN TO THE INVENTOR

Plants of the new cultivar 'SPCDW1711' are similar to the cultivar, *Vanda* 'SPCDW1102' (European Community Plant Variety Rights grant number 33691). A comparison of 'SPCDW1711' with *Vanda* 'SPCDW1102' is described in Table 3.

TABLE 3

| Characteristic | 'SPCDW1711' | 'SPCDW1102' |
|---|---|---|
| General coloration of the petals and sepals when fully opened. | Distinct color contrast between the upper half of the flower, comprised of a purple dorsal sepal, purple lateral petals which are lightly suffused greyed-yellow, and dark greyed-purple lateral sepals. | Distinct color contrast between the upper half of the flower, comprised of a purple dorsal sepal, purple lateral petals, and dark greyed-purple lateral sepals. All petals and sepals are heavily suffused with greyed-yellow |
| Occurrence of colored spots on the dorsal sepal. | No spots present. | Spots present. |
| Occurrence of colored spots on the lateral sepals. | Less densely spotted. | More densely spotted. |
| Occurrence of colored spots on the lateral petals. | Base of the petals are irregularly blotched and finely dotted greyed-purple. | Entire petals are densely blotched and dotted. |

That which is claimed is:

1. A new and distinct variety of *Vanda* plant named 'SPCDW1711', substantially as described and illustrated herein.

* * * * *